United States Patent [19]

Ayen

[11] 4,386,228
[45] May 31, 1983

[54] PROCESS FOR START-UP OF OXYCHLORINATION REACTION

[75] Inventor: Richard J. Ayen, Darien, Conn.

[73] Assignee: Stauffer Chemical Company, Westport, Conn.

[21] Appl. No.: 8,824

[22] Filed: Feb. 2, 1979

Related U.S. Application Data

[63] Continuation-in-part of Ser. No. 844,754, Oct. 25, 1977, abandoned.

[51] Int. Cl.³ .............................................. C07C 17/15
[52] U.S. Cl. .................................... 570/243; 570/224
[58] Field of Search .......... 260/658 R, 659 A, 662 A, 260/654 A; 570/224, 243, 222, 223

[56] References Cited

U.S. PATENT DOCUMENTS

| | | | |
|---|---|---|---|
| 2,966,525 | 12/1960 | Steen | 260/654 A |
| 3,215,508 | 11/1965 | Piester | 260/654 A |
| 3,461,084 | 8/1969 | Li | 260/659 A |
| 3,585,246 | 6/1971 | Van Camp et al. | 260/659 A |

FOREIGN PATENT DOCUMENTS 214293 4/1924 United Kingdom ........... 260/659 A

Primary Examiner—Charles F. Warren
Assistant Examiner—Joseph A. Boska
Attorney, Agent, or Firm—Joel G. Ackerman

[57] ABSTRACT

A process for initiating a fluidized bed process for oxychlorination of methane and/or chlorinated derivatives thereof with hydrogen chloride and air.

6 Claims, 1 Drawing Figure

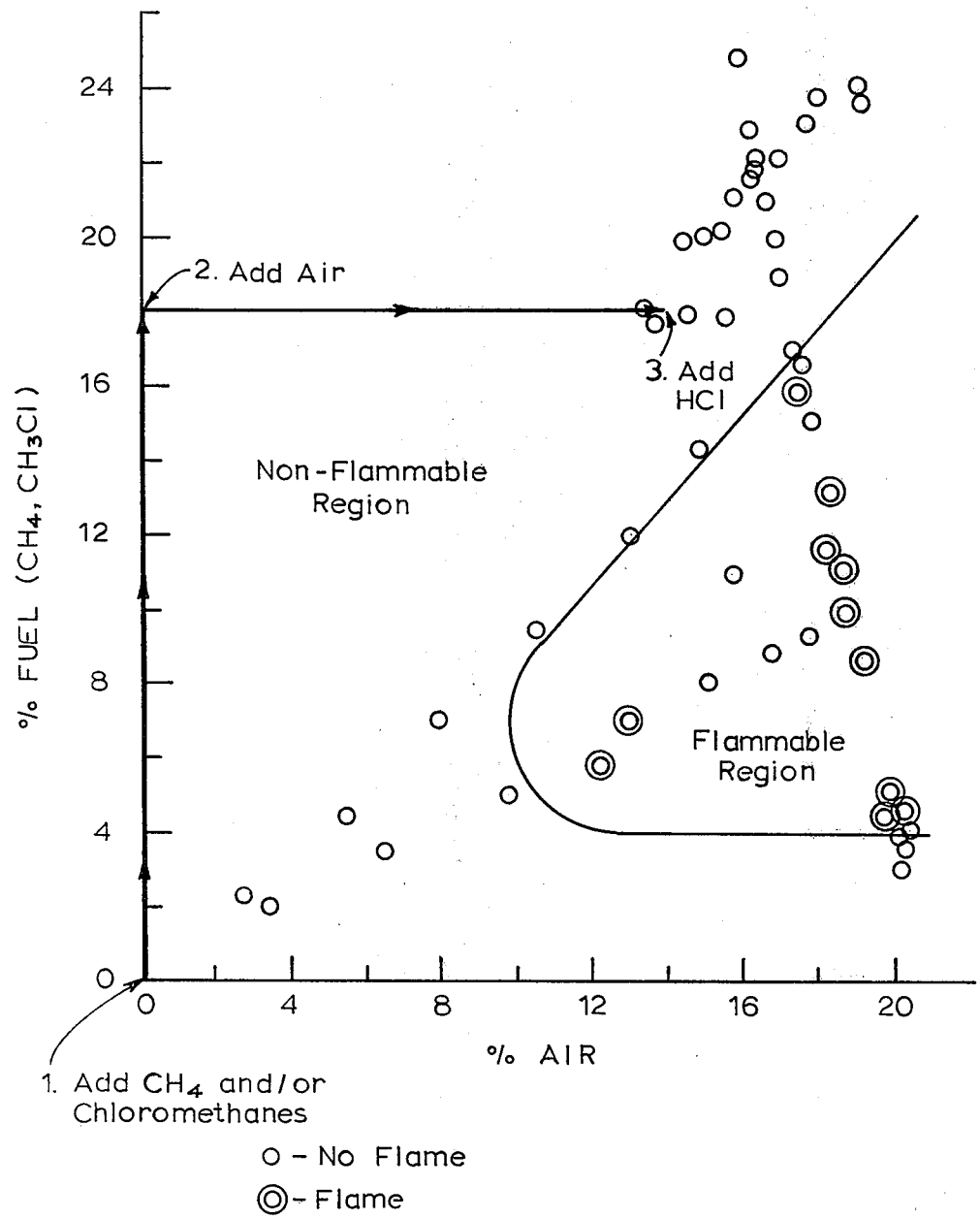

PROCESS FOR START-UP OF OXYCHLORINATION REACTION

CROSS-REFERENCES TO RELATED APPLICATIONS

This is a continuation-in-part of application Ser. No. 844,754, filed Oct. 25, 1977 now abandoned.

BACKGROUND AND PRIOR ART

This invention relates to initiation of a fluidized bed process for oxychlorination of methane, methyl chloride, other chlorinated derivatives of methane such as methylene chloride, chloroform and carbon tetrachloride and/or mixtures thereof by reaction with hydrogen chloride and air, in the presence of an oxychlorination catalyst. Catalysts of this type generally consist of one or more metallic chlorides supported on an appropriate support for use in a fluidized bed. For example, one such catalyst for oxychlorination of methane in a fluidized bed is disclosed in U.S. Pat. No. 3,657,367 of Robert J. Blake, et al.

The start-up of reactions and processes in general, and of oxychlorination processes in particular, is usually a carefully performed matter. It is necessary to introduce the feeds in a controlled manner so as to prevent formation of explosive mixtures, over-reaction, and other undesirable effects which may take place at start-up due to an imbalance of feed or insufficient control of operating conditions. For example, U.S. Pat. No. 3,585,246 of Vancamp, et al., discloses a process of initiating an oxygen-based oxychlorination reaction for hydrocarbons having from 1 to 4 carbon atoms and chlorinated derivatives thereof in which an inert gas or air is first introduced to fluidize the catalyst. Next, the chlorinating agent is admitted to the system in a quantity representing one-half of that normally employed during the oxychlorination reaction. Once the chlorinating agent and the air have had an opportunity to thoroughly mix, the material to be chlorinated is introduced. The bed temperature is then raised to the optimum temperature for the reaction, the air feed is cut out altogether and an oxygen feed gradually introduced until the temperature of the bed has reached the optimum value. As pointed out in the patent, care must be taken to bring the bed temperature up to a temperature at which the particular hydrocarbon being fed will react with the chlorinating agent and maintain this temperature through the initial phase of start-up, otherwise the reaction will die. It is also pointed out that other deviations from the procedure could result in excessive pressure build-up during start-up and may even result in an explosion.

In general, however, there is a risk posed by starting up a methane oxychlorination process by a procedure in which air is introduced before the introduction of the hydrocarbon feed. Such operation results in the environment inside the reactor first consisting of an oxidizing atmosphere; which is then converted to a reducing atmosphere as the hydrocarbon is charged. Passing from an oxidizing atmosphere to a reducing atmosphere increases the risk of formation of a flammable mixture of gases in the reactor. In the process of U.S. Pat. No. 3,585,246 this risk is decreased by introducing the feed directly into the fluidized bed rather than through a wind chest; however, there is still a danger of forming an explosive mixture in the free space above the bed if a quenching of the reaction should occur after both air and hydrocarbon feeds are switched on.

It is an object of the present invention to provide a process for initiation of a reaction comprising oxychlorination of a material to be chlorinated selected from the group consisting of methane, methyl chloride, chlorinated derivatives of methane and mixtures thereof with hydrogen chloride and air.

It is a further object of the present invention to provide a method for initiating such an oxychlorination reaction in which the danger of forming an explosive mixture can be lessened.

Another object of the present invention is to provide a method of initiating such an oxychlorination reaction which permits good control of the start-up procedure.

A further object of the present invention is to provide a method of initiating such an oxychlorination reaction in which the start-up can be conducted at a temperature initially below that required for the conduct of the oxychlorination process itself.

SUMMARY OF THE INVENTION

The invention comprises a method for initiating a continuous oxychlorination process in which a material to be chlorinated selected from the group consisting of (a) methyl chloride, (b) mixtures of two or more chlorinated derivatives of methane, and (c) mixtures of methane and one or more chlorinated derivatives thereof, is contacted with hydrogen chloride and air in a fluidized bed reactor containing a fluidized bed of an oxychlorination catalyst, comprising the steps of:

(a) establishing a bed temperature of between about 150° C. and about 200° C. in the reactor;

(b) introducing a feed consisting essentially of the material to be chlorinated into the reactor;

(c) permitting the reactor to reach stable operating conditions;

(d) introducing either of the air or hydrogen chloride feeds into the reactor;

(e) permitting the reactor to again reach stable operating conditions; and (f) introducing the other of the air and hydrogen chloride feeds into the reactor.

DESCRIPTION OF THE DRAWING

The drawing is a graphical depiction of the flammability of mixtures of methane and/or methyl chloride with air, and refers to the conduct of the process as shown in the Example.

DETAILED DESCRIPTION OF THE INVENTION

The start-up of a methane oxychlorination reaction according to the present invention proceeds as follows:

A suitable catalyst for operation in a fluidized bed is introduced into a fluidized bed reactor in an appropriate amount. The catalyst, for example, comprises cupric chloride on a porous refractory support. It may also contain additives such as alkali metal chlorides, alkaline earth metal chlorides, rare earth metal chlorides, and mixtures thereof, and inert particular diluents. Supports typically utilized are various types of alumina, silica-alumina, silica gel, diatomaceous earth, etc., having an appropriate particle size for use in fluidized beds.

Prior to introducing any of the feeds, the reactor is preferably first heated by external means in the usual manner to a temperature between about 150° C. and about 200° C. During this time air or an inert gas is passed through the catalyst bed to ensure uniform temperature. The air or gas may be heated so as to provide part or all of the heat to the reactor. The reactor is then thoroughly purged with nitrogen gas until the residual oxygen content is less than 1%, to prevent the formation of explosive mixtures when the feed to be chlorinated is introduced, as hereafter discussed. The reaction pressure is then adjusted to the desired value, for example by pinching with a control valve on the reactor exit line or elsewhere downstream. It is also convenient to check the system for leaks at this time.

The first material introduced into the reactor is the material to be chlorinated. This material contains at least one chlorinated derivative of methane, such as methyl chloride, methylene chloride, chloroform or carbon tetrachloride. Of these, methyl chloride is preferred. Thus, the material to be chlorinated may be a mixture of two or more chloromethanes, but is preferably methyl chloride alone, and most preferably a mixture of methane and one or more of its chlorinated derivatives. In conducting start-up operations it is recommended that the total gas flow be approximately constant at all times. The introduction of the material to be chlorinated therefore is accompanied by a corresponding decrease in the volume of nitrogen introduced into the reactor. The introduction of the material to be chlorinated also serves to fluidize the catalyst.

It is possible to introduce a feed consisting entirely of chlorinated derivatives of methane; however, if methyl chloride is not introduced in this feed, there may be an insufficient quantity of hydrogen atoms to generate water necessary for use in hydrolysis Reactions 3 and 4 as well as consumption of phosgene according to Reaction 8, from reactions such as Reaction 1 (see below). This would require adding water to the reactor, for example in the form of steam. However, this is less desirable as steam can cause substantial caking of the fluidized bed catalyst.

A methane oxychlorination process typically is operated at between about 340° C. and about 600° C., preferably between about 370° C. and about 450° C. Methyl chloride oxychlorination is usually conducted at about 340°–390° C. As pointed out in U.S. Pat. No. 3,585,246, it is necessary in starting up such a process to bring the bed temperature up to that at which the reaction will take place, and maintain it at that temperature. However, it has now been found that inclusion of at least one chlorinated derivative of methane in the material to be chlorinated enables the start-up to be conducted at initial bed temperatures of between about 150° C. and about 200° C., which permits better control of the reaction and requires less pre-heating. This is due to the fact that oxidation and/or hydrolysis of the chlorinated derivatives of methane will occur during start-up when the introduction of air is commenced. These reactions are exothermic reactions which produce heat, raising the bed temperature to one at which the oxychlorination reaction will take place.

Among these exothermic reactions which are believed to take place are the following:

$$CH_3Cl + 3/2\ O_2 \rightarrow CO_2 + HCl + H_2O \qquad 1.$$

$$CH_2Cl_2 + O_2 \rightarrow CO_2 + 2HCl \qquad 2.$$

$$CHCl_3 + H_2O + \tfrac{1}{2}O_2 \rightarrow CO_2 + 3HCl \qquad 3.$$

$$CCl_4 + 2H_2O \rightarrow CO_2 + 4HCl\ (hydrolysis) \qquad 4.$$

$$CCl_4 + O_2 \rightarrow COCl_2 + Cl_2 \qquad 5.$$

$$CH_2Cl_2 + 3/2\ O_2 \rightarrow CO_2 + Cl_2 + H_2O \qquad 6.$$

The presence of water, produced by reactions such as Reactions 1 and 6 above, and/or by reaction of methane with oxygen:

$$CH_4 + 2O_2 \rightarrow CO_2 + 2H_2O \qquad 7.$$

is believed to prevent the formation of phosgene (as in Reaction 5, for example) by the following reaction:

$$COCl_2 + H_2O \rightarrow CO_2 + 2HCl \qquad 8.$$

thus producing more hydrogen chloride for use in the oxychlorination reaction.

Once the flow rate of methane and/or chlorinated derivatives thereof has been appropriately adjusted and the temperature and flow rate have been maintained under control for an appropriate period either the hydrogen chloride or the air is then introduced at the desired flow rate with an accompanying decrease in nitrogen flow and the reactor pressure is adjusted if necessary. When the temperature, pressure and flow rates have been stabilized, the remaining feed (hydrogen chloride or air) is introduced at less than the desired flow rate. Heating is continued as required while the flow rate of the last-introduced feed is slowly increased until the desired rate is reached. It is also within the scope of the present invention to introduce the air at less than the desired flow rate for reaction, then introduce the hydrogen chloride gas at the desired flow rate, and then increase the amount of the air up to the desired rate.

Either hydrogen chloride or air can be introduced before the other. What is most essential is that the feed to be chlorinated be introduced into the reactor before either the hydrogen chloride or air. In this manner, an overall reducing atmosphere is maintained in the reactor at all times during start-up, sharply decreasing the likelihood of forming a flammable mixture. On introduction of air into the reactor, the temperature begins to rise as a result of the exothermic oxidation and/or hydrolysis of the chlorinated derivatives of methane. No substantial increase in temperature takes place on introduction of the hydrogen chloride.

The pressurization of the reactor is accomplished as known in the art, for example with nitrogen, before the introduction of the methane and/or chlorinated derivatives thereof, or with the methane and/or chlorinated derivatives thereof itself, before introduction of other materials into the system.

The drawing shows the depiction of the flammable region of a mixture of methane and/or methyl chloride (ordinate) and air (abscissa). As will be seen from the Example which follows, by first introducing the material to be chlorinated, the overall gas composition can be maintained outside the region of flammable mixtures. The origin in the drawing represents the gas composition before any of the feeds have been introduced, i.e. 100% nitrogen. When the material to be chlorinated is added, the change in overall gas composition proceeds along the ordinate, away from the flammable region. Of the materials to be chlorinated, only methane and methyl chloride present a danger of forming flammable mixture with air. The other components of the overall mixture, such as methylene chloride, chloroform, carbon tetrachloride, hydrogen chloride, nitrogen and carbon oxides, are inert in this respect.

EXAMPLE

For example, as shown in the Drawing, beginning with a completely inert gas (essentially 100% nitrogen), at the origin, material to be chlorinated is introduced until the fuel (i.e. methane and/or methyl chloride) component comprises about 18 volume % of the gas entering the reactor. At this point the gas composition is maintained constant until reactor conditions have become stabilized. Then, the air is added, with the amount being steadily increased until the gaseous mixture contains about 14 volume % air. On introduction of the air, the reactions indicated previously as (1)–(8) begin to occur, slowly raising the bed temperature. When reactor conditions have assumed a stable state, the hydrogen chloride is added, with the amount being steadily increased until the desired proportion of reactants has been achieved, and the oxychlorination proceeds in the usual fashion.

No doubt modifications and variations of the disclosed process will be obvious to those skilled in the art. For this reason the invention is not considered to be limited in scope by the above disclosure, but only by the claims which follow.

What is claimed is:

1. A method for initiating a continuous oxychlorination process in which a material to be chlorinated selected from the group consisting of methyl chloride mixtures of two or more chlorinated derivatives of methane, and mixtures of methane and one or more chlorinated derivatives thereof, is contacted with hydrogen chloride and air in a fluidized bed reactor containing a fluidized bed of an oxychlorination catalyst, comprising the steps of:

(a) establishing a bed temperature of between about 150° C. and about 200° C. in the reactor;

(b) introducing a feed consisting essentially of the material to be chlorinated into the reactor;

(c) permitting the reactor to reach stable operating conditions;

(d) introducing either of the air or hydrogen chloride feeds into the reactor in a controlled manner;

(e) permitting the reactor to again reach stable operating conditions; and (f) introducing the other of the air and hydrogen chloride feeds into the reactor in a controlled manner, said introduction of air in step (d) or (f) being done so as to prevent formation of explosive mixtures.

2. A process according to claim 1 wherein the material to be chlorinated comprises a mixture of methane, methyl chloride and chloroform.

3. A process according to claim 1 wherein the material to be chlorinated comprises a mixture of methane, methyl chloride and carbon tetrachloride.

4. A process according to claim 1 wherein air is introduced in step (d) and hydrogen chloride in step (f).

5. A process according to claim 1 wherein the hydrogen chloride is introduced in step (d) and the air in step (f).

6. A process according to claim 4 further comprising introducing air in step (d) at a flow rate below that required for the reaction and increasing the flow rate of the air to the appropriate amount after the introduction of the hydrogen chloride in step (f).

* * * * *